(12) United States Patent
Yamada et al.

(10) Patent No.: US 9,115,051 B2
(45) Date of Patent: Aug. 25, 2015

(54) METHOD FOR PRODUCING POLYAMINE COMPOSITION FROM PLANT

(71) Applicant: TOYOBO CO., LTD., Osaka-shi, Osaka (JP)

(72) Inventors: Chiaki Yamada, Tsuruga (JP); Hiroaki Kitazawa, Tsuruga (JP); Shusaku Yanagidani, Tsuruga (JP)

(73) Assignee: TOYOBO CO., LTD., Osaka-shi (JP)

( * ) Notice: Subject to any disclaimer, the term of this patent is extended or adjusted under 35 U.S.C. 154(b) by 0 days.

(21) Appl. No.: 14/357,677

(22) PCT Filed: Sep. 28, 2012

(86) PCT No.: PCT/JP2012/075178
§ 371 (c)(1),
(2) Date: Jun. 16, 2014

(87) PCT Pub. No.: WO2013/051483
PCT Pub. Date: Apr. 11, 2013

(65) Prior Publication Data
US 2014/0378708 A1 Dec. 25, 2014

(30) Foreign Application Priority Data
Oct. 4, 2011 (JP) .................. 2011-219829

(51) Int. Cl.
*C07C 209/86* (2006.01)
*C07C 211/02* (2006.01)

(52) U.S. Cl.
CPC ............. *C07C 209/86* (2013.01); *C07C 211/02* (2013.01)

(58) Field of Classification Search
CPC ...................................... C07C 209/86
See application file for complete search history.

(56) References Cited

FOREIGN PATENT DOCUMENTS

JP 2007-291027 A 11/2007
JP 2010-263816 A 11/2010

OTHER PUBLICATIONS

Okamoto et al., "Polyamine Content of Ordinary Foodstuffs and Various Fermented Foods", Biosci. Biotech. Biochem., vol. 61, 9, 1997, pp. 1582-1584.
International Search Report dated Dec. 18, 2012 issued in corresponding application No. PCT/JP2012/075178.
Written Opinion of the International Searching Authority dated Dec. 18, 2012 issued in corresponding application No. PCT/JP2012/075178.

*Primary Examiner* — Brian J Davis
(74) *Attorney, Agent, or Firm* — Westerman, Hattori, Daniels & Adrian, LLP

(57) ABSTRACT

A method for producing a polyamine composition with high production efficiency that has a low salt concentration includes (1) a step of treating a plant and/or a processed plant product with ethanol; (2) a step of treating the plant and/or the processed plant product with water; (3) a step of treating the plant and/or the processed plant product under an acidic condition; and (4) a step of separating and collecting a liquid fraction.

13 Claims, 2 Drawing Sheets

METHOD FOR PRODUCING POLYAMINE COMPOSITION FROM PLANT

TECHNICAL FIELD

The present invention relates to a method for producing a polyamine composition from a plant.

BACKGROUND ART

"Polyamine" is a generic name for aliphatic hydrocarbons having two or more primary amino groups, which are natural substances present within living bodies. Twenty or more polyamines have been found. In recent years, various bioactivities of polyamines have been found and polyamines are gaining importance. It is known that polyamines mainly have the following bioactivities: (1) stabilizing nucleic acids or changing the structure of nucleic acids due to the polyamine-nucleic acid interaction; (2) activity of promoting various nucleic-acid synthetic systems; (3) activating protein synthetic systems; (4) stabilizing cell membranes or enhancing membrane permeability to substances; (5) eliminating active oxygen; (6) promoting cell proliferation; and (7) anti-allergic activity. Polyamines or polyamine compositions have come to be applied to health foods, cosmetics, food products, and medical and pharmaceutical products.

The following industrially applicable methods of producing polyamines or polyamine compositions have been disclosed: a preparation method by extraction from fish milt (Patent Literature 1); collection methods by separation from milk or milk material (Patent Literature 2 and Patent Literature 3); and preparation methods by treating yeast cells or yeast culture fluid under acidic conditions (Patent Literature 4 and Patent Literature 5). In addition, the following methods of preparing polyamine compositions from plant material have been studied: extraction methods by treating plant material under acidic conditions (Patent Literature 6 and Patent Literature 7); and a method of producing a polyamine extract by adding a solution of a salt such as sodium chloride, magnesium chloride, or calcium chloride to plant material (Patent Literature 8).

CITATION LIST

Patent Literature

PTL 1: Japanese Unexamined Patent Application Publication No. 8-238094
PTL 2: Japanese Unexamined Patent Application Publication No. 2001-8663
PTL 3: Japanese Unexamined Patent Application Publication No. 2001-95483
PTL 4: Japanese Unexamined Patent Application Publication No. 10-52291
PTL 5: Japanese Unexamined Patent Application Publication No. 2000-245493
PTL 6: Japanese Unexamined Patent Application Publication No. 10-101624
PTL 7: Japanese Unexamined Patent Application Publication No. 2007-291027
PTL 8: Japanese Unexamined Patent Application Publication No. 2010-263816

Non Patent Literature

NPL 1: Plant Cell Physiol., 43(2), 196-206, 2002
NPL 2: J. Nutr. Biochem., 4, 66-70, 1993
NPL 3: Biosci. Biotech. Biochem., 61(9), 1582-1584, 1997

SUMMARY OF INVENTION

Technical Problem

Polyamines or polyamine compositions have been produced from plant material by subjecting the plant material to an extraction step under a strong acidic condition of pH 2 or less and by subjecting the extract to a neutralization step with an alkali solution. However, an acid solution for providing the strong acidic condition and the alkali solution for neutralization are used in large quantities, which naturally results in a high concentration of salt contained in the final polyamine compositions. This has been problematic during addition of the polyamine compositions to health foods, cosmetics, food products, medical and pharmaceutical products, and the like.

In the method of producing a polyamine extract by adding a solution of a salt such as sodium chloride, magnesium chloride, or calcium chloride to plant material (PTL 8), the content of salt contained in the final compositions also becomes high. Thus, the same problem occurs during addition of the compositions to health foods, cosmetics, food products, medical and pharmaceutical products, and the like.

Accordingly, there has been a demand for a method for producing a polyamine composition with high production efficiency that has a low salt concentration and is derived from plant material.

In addition, the extraction step under a strong acidic condition causes corrosion of stainless steel tanks that are commonly used for production, which hampers mass production. Accordingly, there has been a demand for a method for producing a polyamine composition that does not employ a strong acidic condition.

Solution to Problem

The inventors of the present invention performed thorough studies; and, as a result, the inventors have found a way that allows both a method for producing a polyamine having a low salt concentration with high production efficiency and a method for producing a polyamine composition that does not use strong acids. The inventors of the present invention have found that a polyamine composition can be produced by performing an extraction step with water serving as a step performed prior to an extraction step under an acidic condition and by subsequently performing the extraction step under a weak acidic condition.

Plants have a unique problem of having a large amount of polysaccharides, polyphenols, secondary metabolites, and the like, which causes a decrease in the extraction efficiency of polyamine compositions. Accordingly, the inventors performed additional studies. As a result, the inventors have found the following findings: by treating a plant and/or a processed plant product with ethanol prior to extraction steps with water and under a weak acidic condition, the viscosity of the treatment solution is decreased to thereby improve workability and, in addition, polysaccharides, polyphenols, and secondary metabolites, which are not polyamines, are removed so that the polyamine content of the polyamine composition is significantly increased. Thus, the inventors have accomplished the present invention.

Specifically, the present invention provides a method for producing a polyamine composition and a polyamine composition below.

1. A method for producing a polyamine composition, the method including: (1) a step of treating a plant and/or a processed plant product with ethanol; (2) a step of treating the plant and/or the processed plant product with water; (3) a step of treating the plant and/or the processed plant product under an acidic condition; and (4) a step of separating and collecting a liquid fraction.

2. The method for producing a polyamine composition according to 1., further including (5) a step of adjusting pH so as to be in a range of 6.5 to 7.5.

3. The method for producing a polyamine composition according to 1. or 2., wherein, in the step of treating a plant and/or a processed plant product with ethanol, the ethanol has a concentration of 20% (v/v) or more and 90% (v/v) or less.

4. The method for producing a polyamine composition according to any one of 1. to 3., wherein, in the step of treating a plant and/or a processed plant product with ethanol, the ethanol has a concentration of 30% (v/v) or more and 70% (v/v) or less.

5. The method for producing a polyamine composition according to any one of 1. to 4., wherein the step of treating the plant and/or the processed plant product under an acidic condition is a step of treating the plant and/or the processed plant product under an acidic condition at a pH of 3.0 to 6.0.

6. The method for producing a polyamine composition according to any one of 1. to 5., wherein the step of treating the plant and/or the processed plant product under an acidic condition is a step of treating the plant and/or the processed plant product under an acidic condition at a pH of 4.0 to 6.0.

7. The method for producing a polyamine composition according to any one of 1. to 6., wherein the step of treating the plant and/or the processed plant product under an acidic condition is a step of treating the plant and/or the processed plant product with an acidic solution of at least one selected from the group consisting of hydrochloric acid, sulfuric acid, nitric acid, acetic acid, phosphoric acid, citric acid, lactic acid, propionic acid, butyric acid, oxalic acid, malonic acid, succinic acid, fumaric acid, maleic acid, malic acid, tartaric acid, benzoic acid, sulfosalicylic acid, and formic acid.

8. The method for producing a polyamine composition according to 7., wherein the step of treating the plant and/or the processed plant product under an acidic condition is a step of treating the plant and/or the processed plant product with an acidic solution of hydrochloric acid and/or citric acid.

9. The method for producing a polyamine composition according to 8., wherein the step of treating the plant and/or the processed plant product under an acidic condition is a step of treating the plant and/or the processed plant product with an acidic solution of citric acid.

10. The method for producing a polyamine composition according to any one of 1. to 9., wherein the polyamine composition contains at least one compound selected from the group consisting of 1,3-diaminopropane, putrescine, cadaverine, caldine, spermidine, homospermidine, aminopropylcadaverine, thermine, spermine, thermospermine, canavalmine, aminopentylnorspermidine, N,N-bis(aminopropyl)cadaverine, homospermine, caldopentamine, homocaldopentamine, caldohexamine, and homocaldohexamine.

11. The method for producing a polyamine composition according to 10., wherein the polyamine composition contains at least one compound selected from the group consisting of putrescine, cadaverine, spermidine, and spermine.

12. The method for producing a polyamine composition according to any one of 1. to 11., wherein the plant and/or the processed plant product is derived from at least one selected from the group consisting of a wheat seed, a wheat germ, a wheat embryo, a soybean seed, a soybean germ, a soybean embryo, soymilk, and soybean curd refuse.

13. The method for producing a polyamine composition according to 12., wherein the plant and/or the processed plant product is derived from a wheat seed, a wheat germ, a wheat embryo, a soybean seed, a soybean germ, or a soybean embryo.

14. A polyamine composition produced from a plant and/or a processed plant product, wherein a concentration of citric acid or citrate in solid content of the polyamine composition is 5% by weight or less.

Advantageous Effects of Invention

According to the present invention, a polyamine composition can be obtained that has a high polyamine content relative to the solid content and an increase in the production efficiency can be expected. In addition, compared with a method of extracting a polyamine composition from plant material by using water alone, a polyamine composition having a higher polyamine concentration can be obtained; and, compared with a method of extracting a polyamine composition from plant material by using an acidic condition alone, a final polyamine composition having a lower salt concentration can be obtained. In summary, the present invention is unprecedentedly and highly advantageous in that a polyamine composition having a low salt concentration and a high polyamine concentration can be produced.

In addition, extraction is performed not under a strong acidic condition but under a weak acidic condition, so that the corrosion effect on stainless steel due to acid is reduced. As a result, large-volume stainless steel tanks that are commonly used in industry can be used, which allows mass production of a polyamine composition.

DESCRIPTION OF EMBODIMENTS

Figure 1:
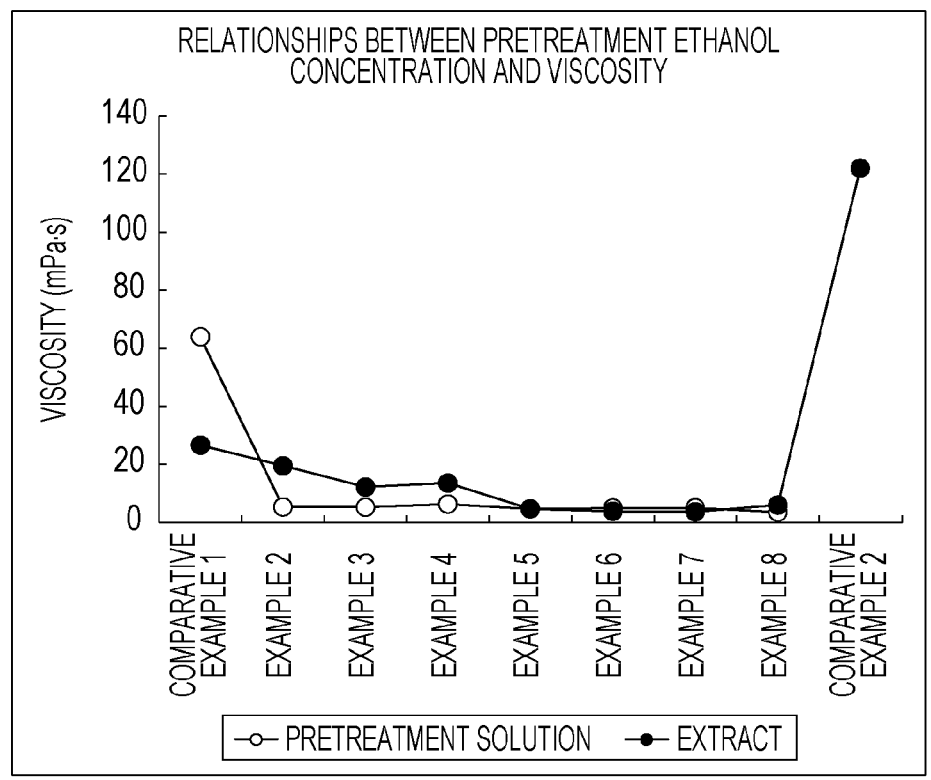
FIG. 1 is a graph illustrating the relationships between ethanol concentration in an ethanol treatment step and viscosity.

The "polyamine composition" denotes a composition containing plant-derived compounds including a polyamine. The polyamine composition may contain, in addition to polyamines, natural components, for example, saccharides such as monosaccharides, oligosaccharides, and polysaccharides, peptides, and proteins. In the present invention, such a composition is referred to as a polyamine composition regardless of whether it has a form of an aqueous solution or a powder. The "solid content" denotes the solute content except for water in the polyamine composition (solution) that is an aqueous solution; and the solid content contains, in addition to polyamines, saccharides, peptides, and salt. In the case where the polyamine composition is a powder, the "solid content" denotes the whole polyamine composition in powder form.

In the present invention, the "plant" denotes a plant body or a plant tissue; and the "processed plant product" denotes a substance obtained by processing a plant body or a plant tissue. The "and/or" means any one or both of the two things.

Various plants and processed plant products can be used. Non-limiting examples include Cucurbitaceous plants, Solanaceous plants, Gramineous plants, Brassicaceous plants, Leguminous plants, Malvaceous plants, Composite plants, Chenopodiaceous plants, Leguminous plants, Theaceous plants, plant extracts of the foregoing, plant essences of the foregoing, and processed products of the foregoing. Specific examples include: sweet potato, tomato, cucumber, squash, melon, watermelon, tobacco, *Arabidopsis thaliana*, green pepper, eggplant, bean, aroid, spinach, carrot, strawberry, potato, rice, corn, alfalfa, wheat, barley, soybean, rape, sorghum, eucalyptus, aspen, kenaf, *Eucommia ulmoides*, sugarcane, sugar beet, cassava, sago palm, chenopod, lily, orchid, carnation, rose, chrysanthemum, petunia, torenia, antirrhinum, cyclamen, gypsophila, geranium, sunflower, lawn grass, cotton, enoki mushroom, shimeji mushroom, matsutake mushroom, shiitake mushroom, mushrooms, ginseng, *Agaricus*, turmeric, Panax ginseng, citruses, banana, kiwi, fruit juice, rice, wheat, barley, soybean, corn, milo, sunflower, germ essence, embryo essence, green tea, black tea, oolong tea, fermented soybeans (natto), soymilk, and soybean curd refuse (okara). Preferably used are Gramineous plants and Leguminous plants.

A plant body or a plant tissue used for producing a polyamine composition is not particularly limited. The plant body or the tissue is preferably in the form of a seed or in a growing period. Examples of the plant body or the tissue in the form of a seed or in a growing period include the whole plant, a flower, a flower bud, an ovary, a fruit, a leaf, a cotyledon, a stem, a bud, a root, a seed, a dry seed, an embryo, a germ, and a root; preferably, a fruit, a leaf, a stem, a bud, a seed, a dry seed, a germ, and an embryo; and particularly preferably, a seed, a dry seed, a germ, and an embryo.

In the present invention, preferably used is a wheat seed, a wheat germ, a wheat embryo, a soybean seed, a soybean germ, a soybean embryo, or a processed plant product that is soymilk or soybean curd refuse, or a combination of the foregoing. More preferably used is a wheat seed, a wheat germ, a wheat embryo, a soybean seed, a soybean germ, or a soybean embryo.

The "step of treating a plant and/or a processed plant product with ethanol" denotes a step of immersing a plant and/or a processed plant product in an ethanol solution and leaving the solution at rest or stirring the solution. As a result of this step, polysaccharides, polyphenols, and secondary metabolites are extracted into ethanol. In the case where grain such as wheat is used as the raw material, gluten that causes an increase in the viscosity is extracted, so that an extract in this step has a low viscosity and the viscosity of an extract in the next step described below can also be reduced. In addition, components other than polyamines are removed to thereby increase the polyamine content relative to the solid content in the final polyamine composition. In this step, the ethanol solution preferably has a concentration of 20% (v/v) or more and 90% (v/v) or less, more preferably 30% (v/v) or more and 70% (v/v) or less. With a concentration of less than 20% (v/v), polysaccharides, polyphenols, secondary metabolites, and the like are not sufficiently extracted to cause an increase in the viscosity and the amount of polyamines extracted becomes large, which are not preferable. On the other hand, with a concentration of more than 90% (v/v), extraction efficiency is decreased and the content of solid content in the polyamine composition is increased, which is also not preferable. The time for the treatment varies depending on the extraction amount, but it is preferably 10 minutes or more, more preferably 30 minutes or more, still more preferably 1 hour or more. In the case where the time is less than 10 minutes, components other than polyamines may be insufficiently extracted in this treatment step. The upper limit of the time is not limited. However, the time is normally 24 hours or less, preferably 12 hours or less, more preferably 6 hours or less.

Polyamines tend not to be extracted into ethanol. Accordingly, after a plant and/or a processed plant product is treated with ethanol, the polyamine content is high not in the liquid fraction but in the plant body residue. Thus, in a preferred embodiment according to the present invention, centrifugal separation and/or filtration separation is performed so that the liquid fraction is separated from the plant body residue and precipitate, and the plant body residue and precipitate are collected and subjected to the next step.

The "step of treating the plant and/or the processed plant product with water" denotes a step of immersing the plant and/or the processed plant product in water to extract a polyamine-containing composition from the plant and/or the processed plant product. The "water" denotes a water that is not mixed with any acid solution or any alkali solution. In this step, the water may be left at rest or stirred. The time for the treatment varies depending on the extraction amount, but it is preferably 10 minutes or more, more preferably 30 minutes or more, still more preferably 1 hour or more. In some cases where the time is less than 10 minutes, a sufficiently large amount of the polyamine composition is not extracted in this treatment step. The upper limit of the time is not limited. However, the time is normally 24 hours or less, preferably 12 hours or less, particularly preferably 6 hours or less. Even when the treatment is performed for 24 hours or more, the extraction amount of the polyamine composition nears saturation and the amount newly extracted thereafter is probably limited.

The "step of treating the plant and/or the processed plant product under an acidic condition" denotes a step of immersing the plant and/or the processed plant product in an acidic solution having a pH of 6 or less and leaving the solution at rest and/or stirring the solution to provide a polyamine-containing extract. In order to decrease the salt concentration of the final composition and in order to suppress corrosion of the stainless steel tank, a weak acidic condition is preferably used. Specifically, the step is preferably performed in the pH range of 3.0 to 6.0, more preferably in the pH range of 4.0 to 6.0. In the present invention, pH is based on a value measured after an acid or an acid solution is added and then leaving at rest or stirring is performed for 10 minutes.

An acidic solution used for the treatment under an acidic condition may be an acidic solution of at least one selected from the group consisting of hydrochloric acid, sulfuric acid, nitric acid, acetic acid, phosphoric acid, citric acid, lactic acid, propionic acid, butyric acid, oxalic acid, malonic acid, succinic acid, fumaric acid, maleic acid, malic acid, tartaric acid, benzoic acid, sulfosalicylic acid, and formic acid. From the standpoint of application to cosmetics, foods, medical and pharmaceutical products, quasi drugs, and animal feed, preferably used is an acidic solution of hydrochloric acid and/or citric acid and particularly preferably used is an acidic solution of citric acid.

The step of treating the plant and/or the processed plant product under an acidic condition is performed by conducting, once or plural times, a process of adding an acid or an acid solution and leaving the solution at rest or stirring the solution. In a preferred embodiment according to the present invention, the step includes conducting, plural times, a process of adding an acid or an acid solution and leaving the solution at rest or stirring the solution. The reason for this is as follows. The amount of an acid or an acid solution added varies depending on the type or amount of the plant or the processed plant product. Accordingly, in order to minimize the amount of an acid or an acid solution added, pH is monitored and the acid or the acid solution is preferably added in plural portions. In addition, a reaction between the acid solution and the plant or the processed plant product results in occurrence of slight neutralization. By adding an acid or an acid solution in small-amount portions, such a neutralization reaction reduces the corrosion action of the acidic solution to stainless steel, so that the load on the stainless steel tank is reduced.

The time for the treatment under an acidic condition can be appropriately set depending on the extraction amount of the polyamine composition; in general, the time is preferably 10 minutes or more, more preferably 30 minutes or more, still more preferably 1 hour or more. In some cases where the time is less than 10 minutes, a sufficiently large amount of the polyamine composition is not extracted in this treatment step. The upper limit of the time is not limited. However, the time is normally 24 hours or less, preferably 12 hours or less, particularly preferably 6 hours or less. Even when the treatment is performed for 24 hours or more, the extraction amount of the polyamine composition nears saturation and the amount newly extracted thereafter is probably limited.

The step of treating the plant and/or the processed plant product under an acidic condition is preferably performed after the step of treating the plant and/or the processed plant product with water. For example, in an embodiment according to the present invention, after the step of treating the plant and/or the processed plant product with water, an acid or an acid solution is added to the aqueous solution to achieve an acidic condition and continuously the step of treating the plant and/or the processed plant product under the acidic condition is performed.

In the present invention, a step of separating and collecting a liquid fraction is included. This step, which is performed after the treatments of the plant and/or the processed plant product with water and under an acidic condition, is a step in which centrifugal separation and/or filtration separation is performed to separate a liquid fraction from plant body residue and precipitate and the liquid fraction is collected. The liquid fraction collected has a high polyamine content and serves as a polyamine composition.

In the present invention, if necessary, a step of adjusting the pH of the acidic-condition solution so as to be in a range of 6.5 to 7.5 is included. This step, which may be performed before or after the step of separating and collecting the liquid fraction, is preferably performed after the step of separating and collecting the liquid fraction. The pH adjustment can be performed by adding an alkali solution. The alkali solution is, for example, a solution of sodium hydroxide, sodium carbonate, sodium hydrogencarbonate, potassium hydroxide, calcium hydroxide, calcium carbonate, barium hydroxide, or ammonia. Sodium hydroxide is preferably used from the standpoint of safety for the human body in terms of salt generated by neutralization.

The polyamine composition is provided in the form of an aqueous solution or a powder. Such a powder of the polyamine composition can be obtained by subjecting the liquid fraction, which is collected by treating a plant and/or a processed plant product with water and under an acidic condition and by performing centrifugal separation or filtration separation, to a treatment by spray drying or vacuum freeze drying.

"Polyamine" in the present invention is a generic name for aliphatic hydrocarbons having two or more primary amino groups, which are natural substances universally present within living bodies. Twenty or more polyamines have been found: for example, 1,3-diaminopropane, putrescine, cadaverine, caldine, spermidine, homospermidine, aminopropylcadaverine, thermine, spermine, thermospermine, canavalmine, aminopentylnorspermidine, N,N-bis(aminopropyl)cadaverine, homospermine, caldopentamine, homocaldopentamine, caldohexamine, and homocaldohexamine. Representative polyamines are putrescine, spermidine, spermine, and cadaverine.

Putrescine is one of representative polyamines, a general natural substance universally present within living bodies, and an aliphatic hydrocarbon compound having two primary amino groups. Cadaverine is one of representative polyamines, a general natural substance universally present within living bodies, and an aliphatic hydrocarbon compound having two primary amino groups. Spermidine is one of representative polyamines, a general natural substance universally present within living bodies, and an aliphatic hydrocarbon compound having three primary amino groups. Spermine is one of representative polyamines, a general natural substance universally present within living bodies, and an aliphatic hydrocarbon compound having four primary amino groups.

If necessary, a polyamine composition may be subjected to a demineralization treatment or a purification treatment by an ion-exchange method, a membrane fractionation method, a gel filtration method, or an electrodialysis method. By performing at least one of these methods, a polyamine composition having a higher purity can be obtained. For example, in the case of the ion-exchange method, a polyamine solution is passed through a column packed with an ion-exchange resin to thereby isolate polyamines from impurities such as amino acids, peptides, proteins, and saccharides. In the ion-exchange resin used, the ion-exchange group may be a sulfonic group, a sulfopropyl group, a phosphate group, a carboxylmethyl group, an aminoethyl group, a diethylamino group, a quaternary aminoethyl group, a quaternary ammonium group, or the like. A cation-exchange resin or an anion-exchange resin may be used. When a cation-exchange resin is used, polyamines are adsorbed onto the cation-exchange resin. Accordingly, non-adsorption substances are sufficiently separated and then polyamines are eluted with an acidic solution such as sulfuric acid or hydrochloric acid or a solution of a salt such as sodium chloride. When an anion-exchange resin is used, polyamines are not adsorbed onto the anion-exchange resin and hence a non-adsorption fraction containing polyamines is collected. For example, in the case of the membrane fractionation method, a polyamine composition is subjected to ultrafiltration (UF) through a UF membrane that is a cellulose-based membrane, a cellulose acetate-based membrane, a polysulfone-based membrane, a polyamide-based membrane, a polyacrylonitrile-based membrane, a polytetrafluoroethylene-based membrane, a polyester-based membrane, a polypropylene-based membrane, or the like, and that has a fractionation molecular-weight range of 1,000 to 100,000, to thereby collect a filtrate containing polyamines. In addition, the polyamine solution is demineralized by being subjected to nanofiltration (NF) through a NF membrane having a salt-blocking percentage of 30% to 80%. For example, in the case of the gel filtration method, a polyamine composition is neutralized and passed through a column packed with gel-filtration carriers to perform fractionation in terms of molecular weight. Thus, polyamines are collected. Such gel-filtration carriers used are dextran-based carriers, acrylamide-based carriers, agarose-based carriers, cellulose-based carriers, polyvinyl-based carriers, glass-based carriers, polystyrene-based carriers, or the like and have a fractionation molecular weight range of 100 to 100,000. For example, in the case of the electrodialysis method, electrodialysis is performed while a polyamine composition and a saline solution are alternately supplied into sections between cation-exchange membranes and anion-exchange membranes. Conditions for electrodialysis include, for example, an initial current density of 0.5 to 15 A/dm2 and a voltage of 0.1 to 1.5 V/tank.

If necessary, the polyamine composition may be mixed with an emulsifying agent such as a sucrose fatty acid ester or a fatty acid ester, crystalline cellulose, enzymatic-degradation dextrin, indigestible dextrin, cluster dextrin, cyclodextrin, maltooligosaccharide, isomaltooligosaccharide, galactooligosaccharide, or the like, which are commonly used as excipients.

The present invention is advantageous in that the necessity of using a polyphenol adsorbent is eliminated. In the existing methods of extracting polyamine compositions from plant material under strong acidic conditions, polyphenol adsorbents are used to thereby collect polyamines or polyamine compositions. The polyphenol adsorbents are substances that can adsorb polyphenols and are, for example, PVPP (polyvinylpolypyrrolidone), PVP (polyvinyl pyrrolidone), and PEG (polyethylene glycol). Obviously, the above description is not intended to exclude use of polyphenol adsorbents in embodiments according to the present invention.

The present invention provides a polyamine composition produced from a plant and/or a processed plant product in which the concentration of citric acid or citrate in the solid content is 5% by weight or less. The present invention provides a polyamine composition having a low salt concentration and a high polyamine concentration. The concentration of citric acid or citrate in the solid content denotes the concentration of citric acid or citrate in the solute and is preferably, relative to the solid content, 5% by weight or less, more preferably 3% by weight or less. In the case where the polyamine composition is a powder, the "solid content" denotes the whole polyamine composition in powder form; and the concentration of citric acid or citrate in the solid content denotes the concentration of citric acid or citrate in the powder.

A polyamine composition according to the present invention can be used by being added to cosmetics, foods, medical and pharmaceutical products, quasi drugs, animal feed, and the like.

EXAMPLES

Hereinafter, the present invention will be specifically described with reference to examples of the present invention. However, the present invention is not limited to these examples.

(Method of Measuring Polyamine Concentration)

The polyamine content of samples was measured by a method described below. Plants contain polyamines in the form of free polyamines, conjugated polyamines, and bound polyamines. All these polyamines can be analyzed (NPLs 1 to 3). However, in the present invention, free polyamines were measured.

(1) A microtube equipped with a screw cap is charged with 20 µl of a sample, 360 µl of exchanged water, 20 µl of an internal standard solution (0.05 nmol/µl, 1,7-diaminoheptane), 200 µL of a saturated aqueous solution of sodium carbonate, and 200 µL of a dansyl chloride/acetone solution (10 mg/mL) and this mixture is mildly mixed. The tube is firmly sealed with the cap and then heated in a water bath at 60° C. for an hour to cause dansylation.

(2) The tube is left to cool. Subsequently, 200 µL of a proline aqueous solution (100 mg/mL) is added and mixed. The tube is again heated in the water bath for 30 minutes.

(3) After the tube is left to cool again, nitrogen gas is blown to remove acetone. Subsequently, 600 µL of toluene is added and the solution is vigorously mixed. The tube is centrifuged to provide two separate phases. Subsequently, the upper toluene layer is taken into a 500 µL microtube. To the taken toluene, nitrogen gas is blown to completely remove toluene. To the microtube, 120 µL of methanol is added to dissolve dansylated free polyamines.

(4) The amount of free polyamines that are putrescine, spermidine, and spermine is analyzed with a high performance liquid chromatography connected to a fluorescence detector (excitation wavelength: 365 nm, emission wavelength: 510 nm) by an internal standard method. The HPLC column used is a µBondapak C18 (manufactured by Waters Corporation: 027324, 3.9×300 mm, particle size: 10 µm). The polyamine contents in the sample are calculated by determining the peak areas of the polyamines and the internal standard from the HPLC charts of the standard solution and the sample.

(Method of Measuring Solid Content Concentration)

The content of solid content in samples was measured by a method described below.

(1) Place an aluminum can in a dryer at 105° C. and dry the aluminum can for an hour.
(2) Leave the aluminum can in a desiccator to cool for 30 minutes and measure the weight of the aluminum can (tare weight).
(3) Place 1 mL of a sample in the aluminum can and measure the weight (sample weight).
(4) Place the aluminum can back into the dryer at 105° C. and perform drying for two hours.
(5) Leave the aluminum can in a desiccator to cool for 30 minutes and subsequently measure the weight (dry weight).
(6) Determine the solid content concentration with the following calculation formula.

Solid content concentration (%)=[(dry weight)−(tare weight)]/(sample weight)×100

Comparative Example 1

(1) Wheat germ (100 g) was mixed with 400 ml of water (ethanol concentration: 0% (v/v)) and stirred under a condition of a water temperature of 25° C. with a mixing device (Three-one Motor, manufactured by HEIDON) at 100 rpm for an hour. After the stirring was completed, viscosity measurement was performed. The viscosity measurement was performed with an oscillation-type viscometer VISCOMATE VM-10A (manufactured by CBC Co., Ltd.).

(2) The solution was then centrifuged under conditions of 12000 rpm and 10 minutes so as to be separated into plant residue and supernatant and the supernatant was collected. The obtained supernatant defined as a pretreatment solution was measured in terms of polyamine concentration and solid content concentration.

(3) The plant residue obtained after the collection of the supernatant was mixed with 400 ml of water and stirred under a condition of a water temperature of 25° C. with the mixing device at 100 rpm for an hour.

(4) After the step (3), the solution was mixed with citric acid (anhydride) and adjusted to a pH of 4.0, and stirred with the mixing device at 100 rpm for an hour.

(5) The solution was again mixed with citric acid (anhydride) so as to be adjusted to a pH of 4.0, and further stirred with the mixing device at 100 rpm for an hour. After the stirring was completed, viscosity measurement was performed as in (1).

(6) The solution was centrifuged under conditions of 12000 rpm and 10 minutes and the supernatant was collected as an extract. The extract was measured in terms of polyamine concentration and solid content concentration.

The results of Comparative example 1 were as follows. The viscosity in the ethanol treatment step was 63.9 mPa·s.

Figure 2:
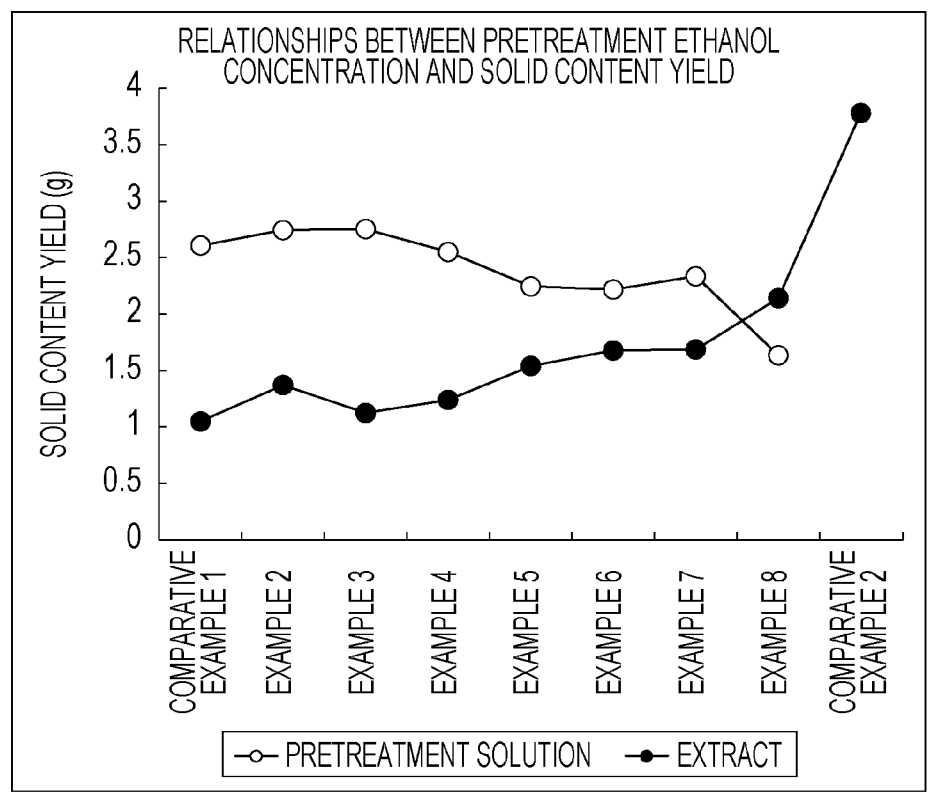
FIG. 2 is a graph illustrating the relationships between ethanol concentration in an ethanol treatment step and solid content yields of a pretreatment solution and an extract.
Figure 3:
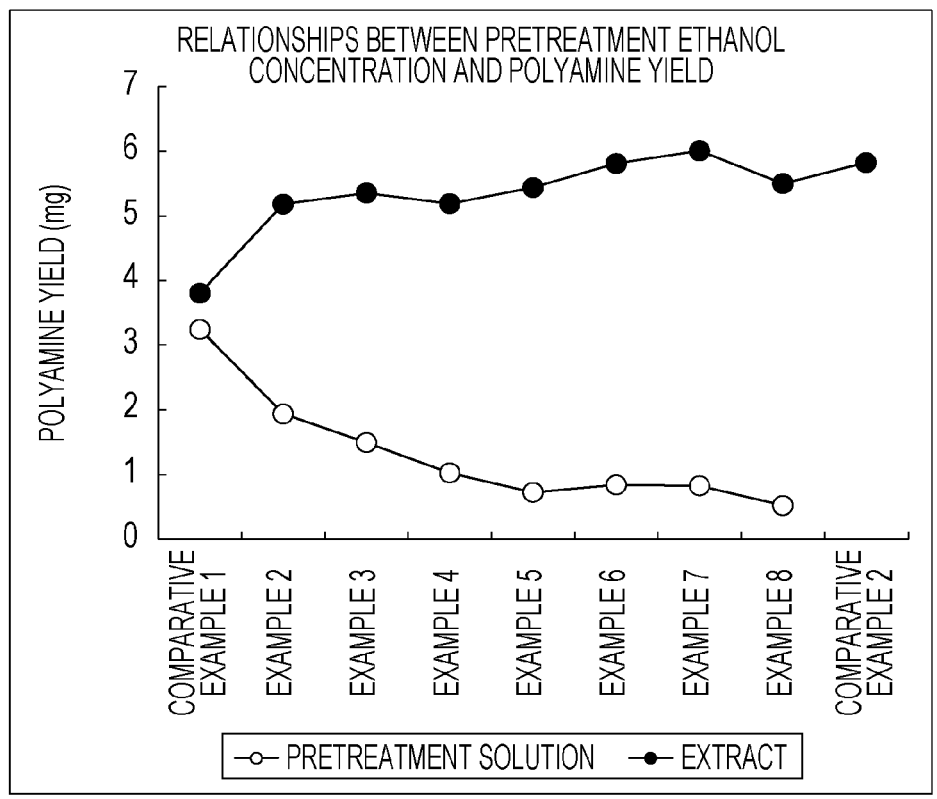
FIG. 3 is a graph illustrating the relationships between ethanol concentration in an ethanol treatment step and polyamine yields of a pretreatment solution and an extract.
Figure 4:
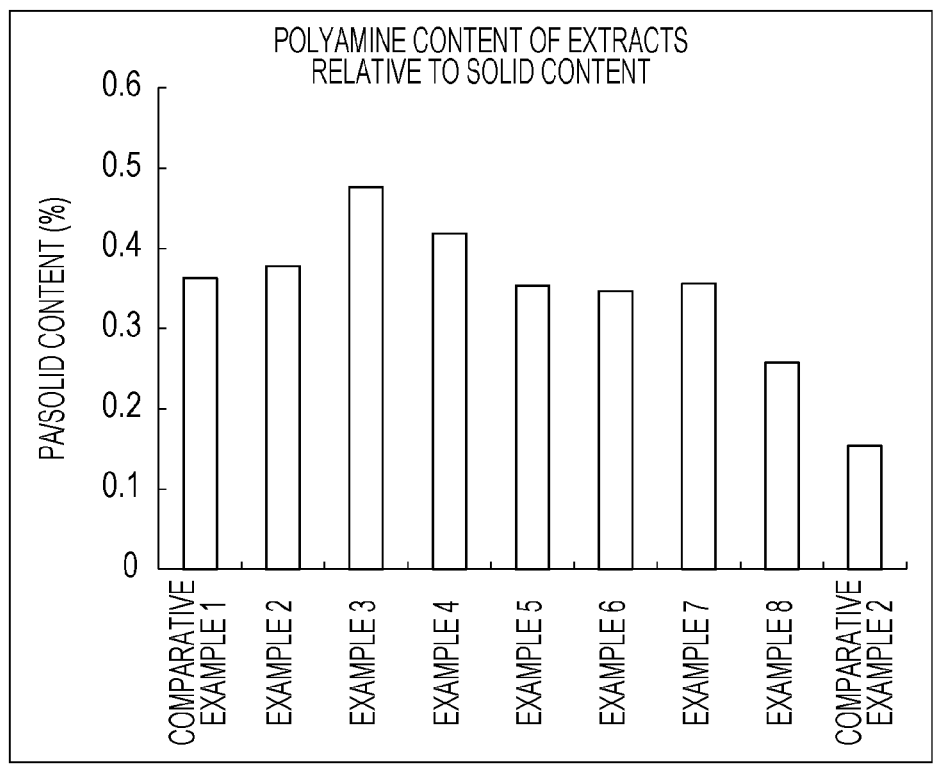
FIG. 4 is a graph illustrating polyamine content of extracts relative to the solid content.

Regarding the pretreatment solution, the polyamine concentration was 0.0108% and the solid content concentration was 8.69%. Regarding the extract, the polyamine concentration was 0.0098%, the solid content concentration 2.69%, and the polyamine concentration relative to the solid content was 0.363%. The results of Comparative examples 1 and 2 and Examples 1 to 7 are described in Table 1 and FIGS. 1 to 4.

Example 1

(1) Wheat germ (100 g) was mixed with 400 ml of an ethanol solution having an ethanol concentration of 20% (v/v) and stirred under a condition of a water temperature of 25° C. with a mixing device (Three-one Motor, manufactured by HEIDON) at 100 rpm for an hour. After the stirring was completed, viscosity measurement was performed. The viscosity measurement was performed with an oscillation-type viscometer VISCOMATE VM-10A (manufactured by CBC Co., Ltd.).
(2) The solution was then centrifuged under conditions of 12000 rpm and 10 minutes so as to be separated into plant residue and supernatant and the supernatant was collected. The obtained supernatant defined as a pretreatment solution was measured in terms of polyamine concentration and solid content concentration.
(3) The plant residue obtained after the collection of the supernatant was mixed with 400 ml of water and stirred under a condition of a water temperature of 25° C. with the mixing device at 100 rpm for an hour.
(4) After the step (3), the solution was mixed with citric acid (anhydride) and adjusted to a pH of 4.0, and stirred with the mixing device at 100 rpm for an hour.
(5) The solution was again mixed with citric acid (anhydride) so as to be adjusted to a pH of 4.0, and further stirred with the mixing device at 100 rpm for an hour. After the stirring was completed, viscosity measurement was performed as in (1).
(6) The solution was centrifuged under conditions of 12000 rpm and 10 minutes and the supernatant was collected as an extract. The extract was measured in terms of polyamine concentration and solid content concentration.

The results of Example 1 were as follows. The viscosity in the ethanol treatment step was 5.29 mPa·s. Regarding the pretreatment solution, the polyamine concentration was 0.0058% and the solid content concentration was 8.19%. Regarding the extract, the polyamine concentration was 0.0146%, the solid content concentration was 3.86%, and the polyamine concentration relative to the solid content was 0.378%. When the polyamine concentration relative to the solid content (PA/solid content) (%) in Comparative example 3 was defined as 100, the increase or decrease ratio of the polyamine concentration relative to the solid content in this Example was 104.3.

Example 2

(1) Wheat germ (100 g) was mixed with 400 ml of an ethanol solution having an ethanol concentration of 30% (v/v) and stirred under a condition of a water temperature of 25° C. with a mixing device (Three-one Motor, manufactured by HEIDON) at 100 rpm for an hour. After the stirring was completed, viscosity measurement was performed. The viscosity measurement was performed with an oscillation-type viscometer VISCOMATE VM-10A (manufactured by CBC Co., Ltd.).
(2) The solution was then centrifuged under conditions of 12000 rpm and 10 minutes so as to be separated into plant residue and supernatant and the supernatant was collected. The obtained supernatant defined as a pretreatment solution was measured in terms of polyamine concentration and solid content concentration.
(3) The plant residue obtained after the collection of the supernatant was mixed with 400 ml of water and stirred under a condition of a water temperature of 25° C. with the mixing device at 100 rpm for an hour.
(4) After the step (3), the solution was mixed with citric acid (anhydride) and adjusted to a pH of 4.0, and stirred with the mixing device at 100 rpm for an hour.
(5) The solution was again mixed with citric acid (anhydride) so as to be adjusted to a pH of 4.0, and further stirred with the mixing device at 100 rpm for an hour. After the stirring was completed, viscosity measurement was performed as in (1).
(6) The solution was centrifuged under conditions of 12000 rpm and 10 minutes and the supernatant was collected as an extract. The extract was measured in terms of polyamine concentration and solid content concentration.

The results of Example 2 were as follows. The viscosity in the ethanol treatment step was 5.24 mPa·s. Regarding the pretreatment solution, the polyamine concentration was 0.0045% and the solid content concentration was 8.34%. Regarding the extract, the polyamine concentration was 0.0147%, the solid content concentration was 3.08%, and the polyamine concentration relative to the solid content was 0.476%. When the polyamine concentration relative to the solid content (PA/solid content) (%) in Comparative example 3 was defined as 100, the increase or decrease ratio of the polyamine concentration relative to the solid content in this Example was 131.4.

Example 3

(1) Wheat germ (100 g) was mixed with 400 ml of an ethanol solution having an ethanol concentration of 40% (v/v) and stirred under a condition of a water temperature of 25° C. with a mixing device (Three-one Motor, manufactured by HEIDON) at 100 rpm for an hour. After the stirring was completed, viscosity measurement was performed. The viscosity measurement was performed with an oscillation-type viscometer VISCOMATE VM-10A (manufactured by CBC Co., Ltd.).
(2) The solution was then centrifuged under conditions of 12000 rpm and 10 minutes so as to be separated into plant residue and supernatant and the supernatant was collected. The obtained supernatant defined as a pretreatment solution was measured in terms of polyamine concentration and solid content concentration.
(3) The plant residue obtained after the collection of the supernatant was mixed with 400 ml of water and stirred under a condition of a water temperature of 25° C. with the mixing device at 100 rpm for an hour.
(4) After the step (3), the solution was mixed with citric acid (anhydride) and adjusted to a pH of 4.0, and stirred with the mixing device at 100 rpm for an hour.
(5) The solution was again mixed with citric acid (anhydride) so as to be adjusted to a pH of 4.0, and further stirred with the mixing device at 100 rpm for an hour. After the stirring was completed, viscosity measurement was performed as in (1).
(6) The solution was centrifuged under conditions of 12000 rpm and 10 minutes and the supernatant was collected as an extract. The extract was measured in terms of polyamine concentration and solid content concentration.

The results of Example 3 were as follows. The viscosity in the ethanol treatment step was 6.32 mPa·s. Regarding the pretreatment solution, the polyamine concentration was 0.0033% and the solid content concentration was 8.09%. Regarding the extract, the polyamine concentration was 0.0144%, the solid content concentration was 3.44%, and the polyamine concentration relative to the solid content was 0.419%. When the polyamine concentration relative to the solid content (PA/solid content) (%) in Comparative example 3 was defined as 100, the increase or decrease ratio of the polyamine concentration relative to the solid content in this Example was 115.4.

Example 4

(1) Wheat germ (100 g) was mixed with 400 ml of an ethanol solution having an ethanol concentration of 50% (v/v) and stirred under a condition of a water temperature of 25° C. with a mixing device (Three-one Motor, manufactured by HEIDON) at 100 rpm for an hour. After the stirring was completed, viscosity measurement was performed. The viscosity measurement was performed with an oscillation-type viscometer VISCOMATE VM-10A (manufactured by CBC Co., Ltd.).
(2) The solution was then centrifuged under conditions of 12000 rpm and 10 minutes so as to be separated into plant residue and supernatant and the supernatant was collected. The obtained supernatant defined as a pretreatment solution was measured in terms of polyamine concentration and solid content concentration.
(3) The plant residue obtained after the collection of the supernatant was mixed with 400 ml of water and stirred under a condition of a water temperature of 25° C. with the mixing device at 100 rpm for an hour.
(4) After the step (3), the solution was mixed with citric acid (anhydride) and adjusted to a pH of 4.0, and stirred with the mixing device at 100 rpm for an hour.
(5) The solution was again mixed with citric acid (anhydride) so as to be adjusted to a pH of 4.0, and further stirred with the mixing device at 100 rpm for an hour. After the stirring was completed, viscosity measurement was performed as in (1).
(6) The solution was centrifuged under conditions of 12000 rpm and 10 minutes and the supernatant was collected as an extract. The extract was measured in terms of polyamine concentration and solid content concentration.

The results of Example 4 were as follows. The viscosity in the ethanol treatment step was 4.65 mPa·s. Regarding the pretreatment solution, the polyamine concentration was 0.0026% and the solid content concentration was 8.02%. Regarding the extract, the polyamine concentration was 0.0133%, the solid content concentration was 3.75%, and the polyamine concentration relative to the solid content was 0.353%. When the polyamine concentration relative to the solid content (PA/solid content) (%) in Comparative example 3 was defined as 100, the increase or decrease ratio of the polyamine concentration relative to the solid content in this Example was 97.5.

Example 5

(1) Wheat germ (100 g) was mixed with 400 ml of an ethanol solution having an ethanol concentration of 60% (v/v) and stirred under a condition of a water temperature of 25° C. with a mixing device (Three-one Motor, manufactured by HEIDON) at 100 rpm for an hour. After the stirring was completed, viscosity measurement was performed. The viscosity measurement was performed with an oscillation-type viscometer VISCOMATE VM-10A (manufactured by CBC Co., Ltd.).
(2) The solution was then centrifuged under conditions of 12000 rpm and 10 minutes so as to be separated into plant residue and supernatant and the supernatant was collected. The obtained supernatant defined as a pretreatment solution was measured in terms of polyamine concentration and solid content concentration.
(3) The plant residue obtained after the collection of the supernatant was mixed with 400 ml of water and stirred under a condition of a water temperature of 25° C. with the mixing device at 100 rpm for an hour.
(4) After the step (3), the solution was mixed with citric acid (anhydride) and adjusted to a pH of 4.0, and stirred with the mixing device at 100 rpm for an hour.
(5) The solution was again mixed with citric acid (anhydride) so as to be adjusted to a pH of 4.0, and further stirred with the mixing device at 100 rpm for an hour. After the stirring was completed, viscosity measurement was performed as in (1).
(6) The solution was centrifuged under conditions of 12000 rpm and 10 minutes and the supernatant was collected as an extract. The extract was measured in terms of polyamine concentration and solid content concentration.

The results of Example 5 were as follows. The viscosity in the ethanol treatment step was 4.93 mPa·s. Regarding the pretreatment solution, the polyamine concentration was 0.0029% and the solid content concentration was 7.64%. Regarding the extract, the polyamine concentration was 0.0134%, the solid content concentration was 3.85%, and the polyamine concentration relative to the solid content was 0.347%. When the polyamine concentration relative to the solid content (PA/solid content) (%) in Comparative example 3 was defined as 100, the increase or decrease ratio of the polyamine concentration relative to the solid content in this Example was 95.6.

Example 6

(1) Wheat germ (100 g) was mixed with 400 ml of an ethanol solution having an ethanol concentration of 70% (v/v) and stirred under a condition of a water temperature of 25° C. with a mixing device (Three-one Motor, manufactured by HEIDON) at 100 rpm for an hour. After the stirring was completed, viscosity measurement was performed. The viscosity measurement was performed with an oscillation-type viscometer VISCOMATE VM-10A (manufactured by CBC Co., Ltd.).
(2) The solution was then centrifuged under conditions of 12000 rpm and 10 minutes so as to be separated into plant residue and supernatant and the supernatant was collected. The obtained supernatant defined as a pretreatment solution was measured in terms of polyamine concentration and solid content concentration.
(3) The plant residue obtained after the collection of the supernatant was mixed with 400 ml of water and stirred under a condition of a water temperature of 25° C. with the mixing device at 100 rpm for an hour.
(4) After the step (3), the solution was mixed with citric acid (anhydride) and adjusted to a pH of 4.0, and stirred with the mixing device at 100 rpm for an hour.
(5) The solution was again mixed with citric acid (anhydride) so as to be adjusted to a pH of 4.0, and further stirred with the mixing device at 100 rpm for an hour. After the stirring was completed, viscosity measurement was performed as in (1).
(6) The solution was centrifuged under conditions of 12000 rpm and 10 minutes and the supernatant was collected as an extract. The extract was measured in terms of polyamine concentration and solid content concentration.

The results of Example 6 were as follows. The viscosity in the ethanol treatment step was 5.03 mPa·s. Regarding the pretreatment solution, the polyamine concentration was 0.0026% and the solid content concentration was 7.30%. Regarding the extract, the polyamine concentration was 0.0150%, the solid content concentration was 4.21%, and the polyamine concentration relative to the solid content was 0.356%. When the polyamine concentration relative to the solid content (PA/solid content) (%) in Comparative example 3 was defined as 100, the increase or decrease ratio of the polyamine concentration relative to the solid content in this Example was 98.3.

Example 7

(1) Wheat germ (100 g) was mixed with 400 ml of an ethanol solution having an ethanol concentration of 90% (v/v) and stirred under a condition of a water temperature of 25° C. with a mixing device (Three-one Motor, manufactured by HEIDON) at 100 rpm for an hour. After the stirring was completed, viscosity measurement was performed. The viscosity measurement was performed with an oscillation-type viscometer VISCOMATE VM-10A (manufactured by CBC Co., Ltd.).
(2) The solution was then centrifuged under conditions of 12000 rpm and 10 minutes so as to be separated into plant residue and supernatant and the supernatant was collected. The obtained supernatant defined as a pretreatment solution was measured in terms of polyamine concentration and solid content concentration.
(3) The plant residue obtained after the collection of the supernatant was mixed with 400 ml of water and stirred under a condition of a water temperature of 25° C. with the mixing device at 100 rpm for an hour.
(4) After the step (3), the solution was mixed with citric acid (anhydride) and adjusted to a pH of 4.0, and stirred with the mixing device at 100 rpm for an hour.
(5) The solution was again mixed with citric acid (anhydride) so as to be adjusted to a pH of 4.0, and further stirred with the mixing device at 100 rpm for an hour. After the stirring was completed, viscosity measurement was performed as in (1).
(6) The solution was centrifuged under conditions of 12000 rpm and 10 minutes and the supernatant was collected as an extract. The extract was measured in terms of polyamine concentration and solid content concentration.

The results of Example 7 were as follows. The viscosity in the ethanol treatment step was 3.56 mPa·s. Regarding the pretreatment solution, the polyamine concentration was 0.0016% and the solid content concentration was 5.03%. Regarding the extract, the polyamine concentration was 0.0152%, the solid content concentration was 5.91%, and the polyamine concentration relative to the solid content was 0.257%. When the polyamine concentration relative to the solid content (PA/solid content) (%) in Comparative example 3 was defined as 100, the increase or decrease ratio of the polyamine concentration relative to the solid content in this Example was 70.9.

Comparative Example 2

(1) Wheat germ (100 g) was mixed with 400 ml of water and stirred under a condition of a water temperature of 25° C. with a mixing device (Three-one Motor, manufactured by HEIDON) at 100 rpm for an hour.
(2) The solution was then mixed with citric acid (anhydride) and adjusted to a pH of 4.0, and stirred with the mixing device at 100 rpm for an hour.
(3) The solution was again mixed with citric acid (anhydride) so as to be adjusted to a pH of 4.0, and further stirred with the mixing device at 100 rpm for an hour. After the stirring was completed, viscosity measurement was performed with an oscillation-type viscometer VISCOMATE VM-10A (manufactured by CBC Co., Ltd.).
(4) The solution was centrifuged under conditions of 12000 rpm and 10 minutes and the supernatant was collected as an extract. The extract was measured in terms of polyamine concentration and solid content concentration.

The results of Comparative example 2 were as follows. Regarding the extract, the polyamine concentration was 0.0194%, the solid content concentration was 12.6%, and the polyamine concentration relative to the solid content was 0.154%. When the polyamine concentration relative to the solid content (PA/solid content) (%) in Comparative example 3 was defined as 100, the increase or decrease ratio of the polyamine concentration relative to the solid content in this example was 42.5.

As is understood from the above-described results, by performing the ethanol treatment step prior to the extraction steps with water and under a weak acidic condition, the viscosity can be significantly decreased, which considerably contributes to enhancement of workability. In addition, compared with the case of not performing the ethanol treatment step, though a considerable increase in the polyamine yield was not observed, significant differences were observed in the solid content concentration of extracts. Thus, it has been demonstrated that the ethanol treatment step and the extraction steps with water and under a weak acidic condition exert a significant effect on an increase in the polyamine content relative to the solid content.

TABLE 1

| | | | Comparative example 1<br>1 | Example 1<br>2 | Example 2<br>3 | Example 3<br>4 | Example 4<br>5 | Example 5<br>6 | Example 6<br>7 | Example 7<br>8 | Comparative example 2<br>9 |
|---|---|---|---|---|---|---|---|---|---|---|---|
| Pretreatment ethanol concentration (%) | | | 0 | 20 | 30 | 40 | 50 | 60 | 70 | 90 | — |
| Pretreatment solution | Viscosity (mPa·s) | | 63.9 | 5.29 | 5.24 | 6.32 | 4.65 | 4.93 | 5.03 | 3.56 | — |
| | Polyamine | Put concentration (%) | 0.0011 | 0.0004 | 0.0003 | 0.0003 | 0.0002 | 0.0002 | 0.0001 | — | — |
| | | Spd concentration (%) | 0.0080 | 0.0044 | 0.0032 | 0.0020 | 0.0013 | 0.0014 | 0.0012 | 0.0008 | — |
| | | Spm concentration (%) | 0.0017 | 0.0009 | 0.0009 | 0.0010 | 0.0011 | 0.0013 | 0.0012 | 0.0008 | — |
| | | Total concentration (%) | 0.0108 | 0.0058 | 0.0045 | 0.0033 | 0.0026 | 0.0029 | 0.0026 | 0.0016 | — |
| | | Yield (mg) | 3.24 | 1.94 | 1.49 | 1.02 | 0.724 | 0.841 | 0.825 | 0.520 | — |
| | Solid content | Concentration (%) | 8.69 | 8.19 | 8.34 | 8.09 | 8.02 | 7.64 | 7.30 | 5.03 | — |
| | | Yield (g) | 2.61 | 2.74 | 2.75 | 2.55 | 2.25 | 2.22 | 2.33 | 1.63 | — |

TABLE 1-continued

|  |  | Comparative example 1 1 | Example 1 2 | Example 2 3 | Example 3 4 | Example 4 5 | Example 5 6 | Example 6 7 | Example 7 8 | Comparative example 2 9 |
|---|---|---|---|---|---|---|---|---|---|---|
| Extract | Viscosity (mPa·s) | 26.6 | 19.5 | 12.2 | 13.6 | 4.68 | 3.82 | 3.64 | 6.01 | 122 |
|  | Polyamine Put concentration (%) | 0.0009 | 0.0013 | 0.0015 | 0.0013 | 0.0013 | 0.0014 | 0.0015 | 0.0015 | 0.0018 |
|  | Spd concentration (%) | 0.0068 | 0.0103 | 0.0103 | 0.0103 | 0.0094 | 0.0094 | 0.0106 | 0.0107 | 0.0136 |
|  | Spm concentration (%) | 0.0020 | 0.0029 | 0.0029 | 0.0028 | 0.0025 | 0.0026 | 0.0029 | 0.0029 | 0.0040 |
|  | Total concentration (%) | 0.0098 | 0.0146 | 0.0147 | 0.0144 | 0.0133 | 0.0134 | 0.0150 | 0.0152 | 0.0194 |
|  | Yield (mg) | 3.81 | 5.18 | 5.35 | 5.19 | 5.44 | 5.81 | 6.01 | 5.50 | 5.83 |
| Solid content | Concentration (%) | 2.69 | 3.86 | 3.08 | 3.44 | 3.75 | 3.85 | 4.21 | 5.91 | 12.6 |
|  | Yield (g) | 1.05 | 1.37 | 1.12 | 1.24 | 1.54 | 1.68 | 1.69 | 2.14 | 3.78 |
| PA/solid content (%) |  | 0.363 | 0.378 | 0.476 | 0.419 | 0.353 | 0.347 | 0.356 | 0.257 | 0.154 |
| Increase or decrease ratio of PA/solid content (%) |  | 100.0 | 104.3 | 131.4 | 115.4 | 97.5 | 95.6 | 98.3 | 70.9 | 42.5 |

Comparative Example 3

(1) Soybean germ (100 g) was mixed with 400 ml of water (ethanol concentration: 0% (v/v)) and stirred under a condition of a water temperature of 25° C. with a mixing device (Three-one Motor, manufactured by HEIDON) at 100 rpm for an hour. After the stirring was completed, viscosity measurement was performed. The viscosity measurement was performed with an oscillation-type viscometer VISCOMATE VM-10A (manufactured by CBC Co., Ltd.).
(2) The solution was then centrifuged under conditions of 12000 rpm and 10 minutes so as to be separated into plant residue and supernatant and the supernatant was collected. The obtained supernatant defined as a pretreatment solution was measured in terms of polyamine concentration and solid content concentration.
(3) The plant residue obtained after the collection of the supernatant was mixed with 400 ml of water and stirred under a condition of a water temperature of 25° C. with the mixing device at 100 rpm for an hour.
(4) After the step (3), the solution was mixed with citric acid (anhydride) and adjusted to a pH of 4.0, and stirred with the mixing device at 100 rpm for an hour.
(5) The solution was again mixed with citric acid (anhydride) so as to be adjusted to a pH of 4.0, and further stirred with the mixing device at 100 rpm for an hour. After the stirring was completed, viscosity measurement was performed as in (1).
(6) The solution was centrifuged under conditions of 12000 rpm and 10 minutes and the supernatant was collected as an extract. The extract was measured in terms of polyamine concentration and solid content concentration.

The results of Comparative example 3 were as follows. The viscosity in the ethanol treatment step was 1.84 mPa·s. Regarding the pretreatment solution, the polyamine concentration was 0.0056% and the solid content concentration was 7.62%. Regarding the extract, the polyamine concentration was 0.0039%, the solid content concentration was 2.65%, and the polyamine concentration relative to the solid content was 0.0369%.

The results of Comparative examples 3 and 4 and Examples 8 to 14 are described in Table 2.

Example 8

(1) Soybean germ (100 g) was mixed with 400 ml of an ethanol solution having an ethanol concentration of 20% (v/v) and stirred under a condition of a water temperature of 25° C. with a mixing device (Three-one Motor, manufactured by HEIDON) at 100 rpm for an hour. After the stirring was completed, viscosity measurement was performed. The viscosity measurement was performed with an oscillation-type viscometer VISCOMATE VM-10A (manufactured by CBC Co., Ltd.).
(2) The solution was then centrifuged under conditions of 12000 rpm and 10 minutes so as to be separated into plant residue and supernatant and the supernatant was collected. The obtained supernatant defined as a pretreatment solution was measured in terms of polyamine concentration and solid content concentration.
(3) The plant residue obtained after the collection of the supernatant was mixed with 400 ml of water and stirred under a condition of a water temperature of 25° C. with the mixing device at 100 rpm for an hour.
(4) After the step (3), the solution was mixed with citric acid (anhydride) and adjusted to a pH of 4.0, and stirred with the mixing device at 100 rpm for an hour.
(5) The solution was again mixed with citric acid (anhydride) so as to be adjusted to a pH of 4.0, and further stirred with the mixing device at 100 rpm for an hour. After the stirring was completed, viscosity measurement was performed as in (1).
(6) The solution was centrifuged under conditions of 12000 rpm and 10 minutes and the supernatant was collected as an extract. The extract was measured in terms of polyamine concentration and solid content concentration.

The results of Example 8 were as follows. The viscosity in the ethanol treatment step was 2.86 mPa·s. Regarding the pretreatment solution, the polyamine concentration was 0.005% and the solid content concentration was 9.67%. Regarding the extract, the polyamine concentration was 0.0051%, the solid content concentration was 2.86%, and the polyamine concentration relative to the solid content was 0.0483%. When the polyamine concentration relative to the solid content (PA/solid content) (%) in Comparative example 3 was defined as 100, the increase or decrease ratio of the polyamine concentration relative to the solid content in this Example was 131.0.

Example 9

(1) Soybean germ (100 g) was mixed with 400 ml of an ethanol solution having an ethanol concentration of 30% (v/v) and stirred under a condition of a water temperature of 25° C. with a mixing device (Three-one Motor, manufactured by HEIDON) at 100 rpm for an hour. After the stirring was completed, viscosity measurement was performed. The viscosity measurement was performed with an oscillation-type viscometer VISCOMATE VM-10A (manufactured by CBC Co., Ltd.).
(2) The solution was then centrifuged under conditions of 12000 rpm and 10 minutes so as to be separated into plant residue and supernatant and the supernatant was collected. The obtained supernatant defined as a pretreatment solution was measured in terms of polyamine concentration and solid content concentration.
(3) The plant residue obtained after the collection of the supernatant was mixed with 400 ml of water and stirred under a condition of a water temperature of 25° C. with the mixing device at 100 rpm for an hour.
(4) After the step (3), the solution was mixed with citric acid (anhydride) and adjusted to a pH of 4.0, and stirred with the mixing device at 100 rpm for an hour.
(5) The solution was again mixed with citric acid (anhydride) so as to be adjusted to a pH of 4.0, and further stirred with the mixing device at 100 rpm for an hour. After the stirring was completed, viscosity measurement was performed as in (1).
(6) The solution was centrifuged under conditions of 12000 rpm and 10 minutes and the supernatant was collected as an extract. The extract was measured in terms of polyamine concentration and solid content concentration.

The results of Example 9 were as follows. The viscosity in the ethanol treatment step was 3.28 mPa·s. Regarding the pretreatment solution, the polyamine concentration was 0.022% and the solid content concentration was 8.19%. Regarding the extract, the polyamine concentration was 0.0047%, the solid content concentration was 2.81%, and the polyamine concentration relative to the solid content was 0.0439%. When the polyamine concentration relative to the solid content (PA/solid content) (%) in Comparative example 3 was defined as 100, the increase or decrease ratio of the polyamine concentration relative to the solid content in this Example was 118.9.

Example 10

(1) Soybean germ (100 g) was mixed with 400 ml of an ethanol solution having an ethanol concentration of 40% (v/v) and stirred under a condition of a water temperature of 25° C. with a mixing device (Three-one Motor, manufactured by HEIDON) at 100 rpm for an hour. After the stirring was completed, viscosity measurement was performed. The viscosity measurement was performed with an oscillation-type viscometer VISCOMATE VM-10A (manufactured by CBC Co., Ltd.).
(2) The solution was then centrifuged under conditions of 12000 rpm and 10 minutes so as to be separated into plant residue and supernatant and the supernatant was collected. The obtained supernatant defined as a pretreatment solution was measured in terms of polyamine concentration and solid content concentration.
(3) The plant residue obtained after the collection of the supernatant was mixed with 400 ml of water and stirred under a condition of a water temperature of 25° C. with the mixing device at 100 rpm for an hour.
(4) After the step (3), the solution was mixed with citric acid (anhydride) and adjusted to a pH of 4.0, and stirred with the mixing device at 100 rpm for an hour.
(5) The solution was again mixed with citric acid (anhydride) so as to be adjusted to a pH of 4.0, and further stirred with the mixing device at 100 rpm for an hour. After the stirring was completed, viscosity measurement was performed as in (1).
(6) The solution was centrifuged under conditions of 12000 rpm and 10 minutes and the supernatant was collected as an extract. The extract was measured in terms of polyamine concentration and solid content concentration.

The results of Example 10 were as follows. The viscosity in the ethanol treatment step was 3.53 mPa·s. Regarding the pretreatment solution, the polyamine concentration was 0.0020% and the solid content concentration was 8.50%. Regarding the extract, the polyamine concentration was 0.0047%, the solid content concentration was 2.82%, and the polyamine concentration relative to the solid content was 0.0446%. When the polyamine concentration relative to the solid content (PA/solid content) (%) in Comparative example 3 was defined as 100, the increase or decrease ratio of the polyamine concentration relative to the solid content in this Example was 121.0.

Example 11

(1) Soybean germ (100 g) was mixed with 400 ml of an ethanol solution having an ethanol concentration of 50% (v/v) and stirred under a condition of a water temperature of 25° C. with a mixing device (Three-one Motor, manufactured by HEIDON) at 100 rpm for an hour. After the stirring was completed, viscosity measurement was performed. The viscosity measurement was performed with an oscillation-type viscometer VISCOMATE VM-10A (manufactured by CBC Co., Ltd.).
(2) The solution was then centrifuged under conditions of 12000 rpm and 10 minutes so as to be separated into plant residue and supernatant and the supernatant was collected. The obtained supernatant defined as a pretreatment solution was measured in terms of polyamine concentration and solid content concentration.
(3) The plant residue obtained after the collection of the supernatant was mixed with 400 ml of water and stirred under a condition of a water temperature of 25° C. with the mixing device at 100 rpm for an hour.
(4) After the step (3), the solution was mixed with citric acid (anhydride) and adjusted to a pH of 4.0, and stirred with the mixing device at 100 rpm for an hour.
(5) The solution was again mixed with citric acid (anhydride) so as to be adjusted to a pH of 4.0, and further stirred with the mixing device at 100 rpm for an hour. After the stirring was completed, viscosity measurement was performed as in (1).
(6) The solution was centrifuged under conditions of 12000 rpm and 10 minutes and the supernatant was collected as an extract. The extract was measured in terms of polyamine concentration and solid content concentration.

The results of Example 11 were as follows. The viscosity in the ethanol treatment step was 3.61 mPa·s. Regarding the pretreatment solution, the polyamine concentration was 0.0017% and the solid content concentration was 7.86%. Regarding the extract, the polyamine concentration was 0.0052%, the solid content concentration was 3.08%, and the polyamine concentration relative to the solid content was 0.0467%. When the polyamine concentration relative to the solid content (PA/solid content) (%) in Comparative example 3 was defined as 100, the increase or decrease ratio of the polyamine concentration relative to the solid content in this Example was 126.6.

Example 12

(1) Soybean germ (100 g) was mixed with 400 ml of an ethanol solution having an ethanol concentration of 60% (v/v) and stirred under a condition of a water temperature of 25° C. with a mixing device (Three-one Motor, manufactured by HEIDON) at 100 rpm for an hour. After the stirring was completed, viscosity measurement was performed. The viscosity measurement was performed with an oscillation-type viscometer VISCOMATE VM-10A (manufactured by CBC Co., Ltd.).
(2) The solution was then centrifuged under conditions of 12000 rpm and 10 minutes so as to be separated into plant residue and supernatant and the supernatant was collected. The obtained supernatant defined as a pretreatment solution was measured in terms of polyamine concentration and solid content concentration.
(3) The plant residue obtained after the collection of the supernatant was mixed with 400 ml of water and stirred under a condition of a water temperature of 25° C. with the mixing device at 100 rpm for an hour.
(4) After the step (3), the solution was mixed with citric acid (anhydride) and adjusted to a pH of 4.0, and stirred with the mixing device at 100 rpm for an hour.
(5) The solution was again mixed with citric acid (anhydride) so as to be adjusted to a pH of 4.0, and further stirred with the mixing device at 100 rpm for an hour. After the stirring was completed, viscosity measurement was performed as in (1).
(6) The solution was centrifuged under conditions of 12000 rpm and 10 minutes and the supernatant was collected as an extract. The extract was measured in terms of polyamine concentration and solid content concentration.

The results of Example 12 were as follows. The viscosity in the ethanol treatment step was 3.14 mPa·s. Regarding the pretreatment solution, the polyamine concentration was 0.0015% and the solid content concentration was 5.09%. Regarding the extract, the polyamine concentration was 0.0064%, the solid content concentration was 3.92%, and the polyamine concentration relative to the solid content was 0.0494%. When the polyamine concentration relative to the solid content (PA/solid content) (%) in Comparative example 3 was defined as 100, the increase or decrease ratio of the polyamine concentration relative to the solid content in this Example was 134.1.

Example 13

(1) Soybean germ (100 g) was mixed with 400 ml of an ethanol solution having an ethanol concentration of 70% (v/v) and stirred under a condition of a water temperature of 25° C. with a mixing device (Three-one Motor, manufactured by HEIDON) at 100 rpm for an hour. After the stirring was completed, viscosity measurement was performed. The viscosity measurement was performed with an oscillation-type viscometer VISCOMATE VM-10A (manufactured by CBC Co., Ltd.).
(2) The solution was then centrifuged under conditions of 12000 rpm and 10 minutes so as to be separated into plant residue and supernatant and the supernatant was collected. The obtained supernatant defined as a pretreatment solution was measured in terms of polyamine concentration and solid content concentration.
(3) The plant residue obtained after the collection of the supernatant was mixed with 400 ml of water and stirred under a condition of a water temperature of 25° C. with the mixing device at 100 rpm for an hour.
(4) After the step (3), the solution was mixed with citric acid (anhydride) and adjusted to a pH of 4.0, and stirred with the mixing device at 100 rpm for an hour.
(5) The solution was again mixed with citric acid (anhydride) so as to be adjusted to a pH of 4.0, and further stirred with the mixing device at 100 rpm for an hour. After the stirring was completed, viscosity measurement was performed as in (1).
(6) The solution was centrifuged under conditions of 12000 rpm and 10 minutes and the supernatant was collected as an extract. The extract was measured in terms of polyamine concentration and solid content concentration.

The results of Example 13 were as follows. The viscosity in the ethanol treatment step was 2.86 mPa·s. Regarding the pretreatment solution, the polyamine concentration was 0.0008% and the solid content concentration was 3.59%. Regarding the extract, the polyamine concentration was 0.0078%, the solid content concentration was 5.04%, and the polyamine concentration relative to the solid content was 0.0504%. When the polyamine concentration relative to the solid content (PA/solid content) (%) in Comparative example 3 was defined as 100, the increase or decrease ratio of the polyamine concentration relative to the solid content in this Example was 136.6.

Example 14

(1) Soybean germ (100 g) was mixed with 400 ml of an ethanol solution having an ethanol concentration of 90% (v/v) and stirred under a condition of a water temperature of 25° C. with a mixing device (Three-one Motor, manufactured by HEIDON) at 100 rpm for an hour. After the stirring was completed, viscosity measurement was performed. The viscosity measurement was performed with an oscillation-type viscometer VISCOMATE VM-10A (manufactured by CBC Co., Ltd.).
(2) The solution was then centrifuged under conditions of 12000 rpm and 10 minutes so as to be separated into plant residue and supernatant and the supernatant was collected. The obtained supernatant defined as a pretreatment solution was measured in terms of polyamine concentration and solid content concentration.
(3) The plant residue obtained after the collection of the supernatant was mixed with 400 ml of water and stirred under a condition of a water temperature of 25° C. with the mixing device at 100 rpm for an hour.
(4) After the step (3), the solution was mixed with citric acid (anhydride) and adjusted to a pH of 4.0, and stirred with the mixing device at 100 rpm for an hour.
(5) The solution was again mixed with citric acid (anhydride) so as to be adjusted to a pH of 4.0, and further stirred with the mixing device at 100 rpm for an hour. After the stirring was completed, viscosity measurement was performed as in (1).
(6) The solution was centrifuged under conditions of 12000 rpm and 10 minutes and the supernatant was collected as an extract. The extract was measured in terms of polyamine concentration and solid content concentration.

The results of Example 14 were as follows. The viscosity in the ethanol treatment step was 1.96 mPa·s. Regarding the pretreatment solution, the polyamine concentration was 0.0000% and the solid content concentration was 0.34%.

Regarding the extract, the polyamine concentration was 0.0094%, the solid content concentration was 7.09%, and the polyamine concentration relative to the solid content was 0.257%. When the polyamine concentration relative to the solid content (PA/solid content) (%) in Comparative example 3 was defined as 100, the increase or decrease ratio of the polyamine concentration relative to the solid content in this Example was 128.6.

Comparative Example 4

(1) Soybean germ (100 g) was mixed with 400 ml of water and stirred under a condition of a water temperature of 25° C. with a mixing device (Three-one Motor, manufactured by HEIDON) at 100 rpm for an hour.
(2) The solution was then mixed with citric acid (anhydride) and adjusted to a pH of 4.0, and stirred with the mixing device at 100 rpm for an hour.
(4) The solution was again mixed with citric acid (anhydride) so as to be adjusted to a pH of 4.0, and further stirred with the mixing device at 100 rpm for an hour. After the stirring was completed, viscosity measurement was performed with an oscillation-type viscometer VISCOMATE VM-10A (manufactured by CBC Co., Ltd.).
(5) The solution was centrifuged under conditions of 12000 rpm and 10 minutes and the supernatant was collected as an extract. The extract was measured in terms of polyamine concentration and solid content concentration.

The results of Comparative example 4 were as follows. Regarding the extract, the polyamine concentration was 0.0051%, the solid content concentration was 9.32%, and the polyamine concentration relative to the solid content was 0.0203%. When the polyamine concentration relative to the solid content (PA/solid content) (%) in Comparative example 3 was defined as 100, the increase or decrease ratio of the polyamine concentration relative to the solid content in this example was 55.0.

Regarding soybean germ, a significant decrease in the viscosity was not observed, the decrease being achieved by performing the ethanol treatment step prior to the extraction steps with water and under a weak acidic condition. This is probably because gluten, which is contained with a high content in wheat and the like, is substantially not contained in soybeans. However, regarding the final polyamine composition, compared with the case of performing only the treatments with water and under a weak acidic condition and the case of performing extraction with the weak acid alone, the ethanol treatment step and the extraction steps with water and under a weak acidic condition exerted a significant effect on an increase in the polyamine content relative to the solid content.

TABLE 2

| | | | Comparative example 3 | Example 8 | Example 9 | Example 10 | Example 11 | Example 12 | Example 13 | Example 14 | Comparative example 4 |
|---|---|---|---|---|---|---|---|---|---|---|---|
| Pretreatment ethanol concentration (%) | | | 0 | 20 | 30 | 40 | 50 | 60 | 70 | 90 | — |
| Pre-treatment solution | Viscosity | | 1.84 | 2.86 | 3.28 | 3.53 | 3.61 | 3.14 | 2.86 | 1.96 | |
| | Polyamine | Put concentration (%) | 0 | 0.00012 | 0 | 0 | 0 | 0 | 0 | 0 | |
| | | Spd concentration (%) | 0.0043 | 0.0024 | 0.0015 | 0.0014 | 0.0013 | 0.0010 | 0.0003 | 0.0000 | |
| | | Spm concentration (%) | 0.0014 | 0.0003 | 0.0007 | 0.0006 | 0.0005 | 0.0005 | 0.0004 | 0.0000 | |
| | | Total concentration (%) | 0.0056 | 0.0029 | 0.0022 | 0.0020 | 0.0017 | 0.0015 | 0.0008 | 0.0000 | |
| | | Yield (mg) | 0.014 | 0.005 | 0.005 | 0.005 | 0.004 | 0.004 | 0.002 | 0.000 | |
| | Solid content | Concentration (%) | 7.62 | 9.67 | 8.19 | 8.50 | 7.86 | 5.09 | 3.59 | 0.34 | |
| | | Yield (g) | 19.66 | 17.03 | 18.84 | 19.37 | 18.31 | 14.00 | 9.91 | 1.00 | |
| Post-treatment solution | Viscosity | | 1.65 | 1.73 | 1.84 | 1.95 | 2.05 | 2.14 | 2.05 | 2.00 | 2.00 |
| | Polyamine | Put concentration (%) | 0.0000 | 0.0000 | 0.0000 | 0.0000 | 0.0000 | 0.0001 | 0.0001 | 0.0002 | 0.0001 |
| | | Spd concentration (%) | 0.0032 | 0.0042 | 0.0039 | 0.0039 | 0.0043 | 0.0052 | 0.0063 | 0.0074 | 0.0040 |
| | | Spm concentration (%) | 0.0007 | 0.0009 | 0.0008 | 0.0008 | 0.0008 | 0.0011 | 0.0014 | 0.0018 | 0.0010 |
| | | Total concentration (%) | 0.0039 | 0.0051 | 0.0047 | 0.0047 | 0.0052 | 0.0064 | 0.0078 | 0.0094 | 0.0051 |
| | | Yield (mg) | 0.016 | 0.019 | 0.018 | 0.017 | 0.019 | 0.021 | 0.024 | 0.026 | 0.014 |
| | Solid content | Concentration (%) | 2.65 | 2.86 | 2.81 | 2.82 | 3.08 | 3.92 | 5.04 | 7.09 | 9.32 |
| | | Yield (g) | 10.63 | 10.65 | 10.70 | 10.44 | 11.07 | 12.93 | 15.43 | 19.82 | 25.00 |
| | PA/solid content (%) | | 0.0369 | 0.0483 | 0.0439 | 0.0446 | 0.0467 | 0.0494 | 0.0504 | 0.0474 | 0.0203 |
| Increase or decrease ratio of PA/solid content (%) | | | 100.0 | 131.0 | 118.9 | 121.0 | 126.6 | 134.1 | 136.6 | 128.6 | 55.0 |

INDUSTRIAL APPLICABILITY

A polyamine composition according to the present invention has a low salt concentration and is useful in terms of addition to foods, cosmetics, medical and pharmaceutical products, quasi drugs, animal feed, and the like. In addition, the present invention allows use of large-scale stainless steel tanks that are used for industrial production of chemical products, which allows mass production and is advantageous.

The invention claimed is:

1. A method for producing a polyamine composition, the method comprising: (1) a step of treating a plant and/or a processed plant product with ethanol; (2) a step of treating the plant and/or the processed plant product with water; (3) a step of treating the plant and/or the processed plant product under an acidic condition; and (4) a step of separating and collecting a liquid fraction.

2. The method for producing a polyamine composition according to claim 1, further comprising (5) a step of adjusting pH so as to be in a range of 6.5 to 7.5.

3. The method for producing a polyamine composition according to claim 1, wherein, in the step of treating a plant and/or a processed plant product with ethanol, the ethanol has a concentration of 20% (v/v) or more and 90% (v/v) or less.

4. The method for producing a polyamine composition according to claim 1, wherein, in the step of treating a plant and/or a processed plant product with ethanol, the ethanol has a concentration of 30% (v/v) or more and 70% (v/v) or less.

5. The method for producing a polyamine composition according to claim 1, wherein the step of treating the plant and/or the processed plant product under an acidic condition is a step of treating the plant and/or the processed plant product under an acidic condition at a pH of 3.0 to 6.0.

6. The method for producing a polyamine composition according to claim 1, wherein the step of treating the plant and/or the processed plant product under an acidic condition is a step of treating the plant and/or the processed plant product under an acidic condition at a pH of 4.0 to 6.0.

7. The method for producing a polyamine composition according to claim 1, wherein the step of treating the plant and/or the processed plant product under an acidic condition is a step of treating the plant and/or the processed plant product with an acidic solution of at least one selected from the group consisting of hydrochloric acid, sulfuric acid, nitric acid, acetic acid, phosphoric acid, citric acid, lactic acid, propionic acid, butyric acid, oxalic acid, malonic acid, succinic acid, fumaric acid, maleic acid, malic acid, tartaric acid, benzoic acid, sulfosalicylic acid, and formic acid.

8. The method for producing a polyamine composition according to claim 7, wherein the step of treating the plant and/or the processed plant product under an acidic condition is a step of treating the plant and/or the processed plant product with an acidic solution of hydrochloric acid and/or citric acid.

9. The method for producing a polyamine composition according to claim 8, wherein the step of treating the plant and/or the processed plant product under an acidic condition is a step of treating the plant and/or the processed plant product with an acidic solution of citric acid.

10. The method for producing a polyamine composition according to claim 1, wherein the polyamine composition contains at least one compound selected from the group consisting of 1,3-diaminopropane, putrescine, cadaverine, caldine, spermidine, homospermidine, aminopropylcadaverine, thermine, spermine, thermospermine, canavalmine, aminopentylnorspermidine, N,N-bis(aminopropyl)cadaverine, homospermine, caldopentamine, homocaldopentamine, caldohexamine, and homocaldohexamine.

11. The method for producing a polyamine composition according to claim 10, wherein the polyamine composition contains at least one compound selected from the group consisting of putrescine, cadaverine, spermidine, and spermine.

12. The method for producing a polyamine composition according to claim 1, wherein the plant and/or the processed plant product is derived from at least one selected from the group consisting of a wheat seed, a wheat germ, a wheat embryo, a soybean seed, a soybean germ, a soybean embryo, soymilk, and soybean curd refuse.

13. The method for producing a polyamine composition according to claim 12, wherein the plant and/or the processed plant product is derived from a wheat seed, a wheat germ, a wheat embryo, a soybean seed, a soybean germ, or a soybean embryo.

* * * * *